United States Patent [19]

Evans

[11] 4,302,579
[45] Nov. 24, 1981

[54] OPTICAL BRIGHTENING AGENTS AND PHOTOGRAPHIC MATERIALS WHICH CONTAIN THESE BRIGHTENING AGENTS

[75] Inventor: Graham Evans, Galleywood, England

[73] Assignee: Ciba-Geigy AG, Basel, Switzerland

[21] Appl. No.: 171,869

[22] Filed: Jul. 24, 1980

[30] Foreign Application Priority Data

Aug. 21, 1979 [GB] United Kingdom ............... 29033/79

[51] Int. Cl.³ .......................................... C07D 403/10
[52] U.S. Cl. .................................... 542/461; 430/523
[58] Field of Search ........................ 542/461; 430/523

[56] References Cited

U.S. PATENT DOCUMENTS

| 2,713,046 | 7/1955 | Williams et al. | 542/461 |
| 3,371,089 | 2/1968 | Gold et al. | 542/461 |
| 3,558,611 | 1/1971 | Fleck | 542/461 |
| 3,615,544 | 10/1971 | Amano et al. | 96/82 |

FOREIGN PATENT DOCUMENTS 1402877  8/1975  United Kingdom .

Primary Examiner—Arthur P. Demers
Attorney, Agent, or Firm—Sprung, Felfe, Horn, Lynch & Kramer

[57] ABSTRACT

New optical brightening agents and photographic materials which contain in at least one layer these brightening agents are provided. The compounds have the general formula

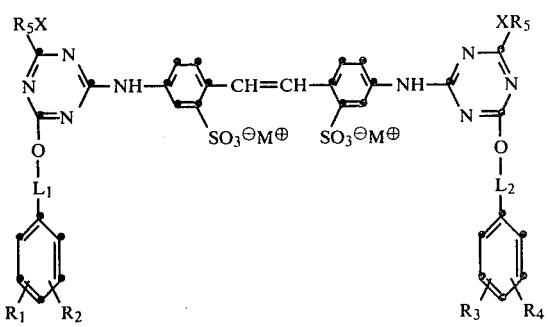

wherein $R_1$ and $R_3$ are hydrogen or methyl, $R_2$ and $R_4$ are alkyl $R_5$ is hydrogen, alkyl, aryl, aralkyl, X is —NH—, —O— or —S—, $L_1$ and $L_2$ are alkylene oxide chains and $M^\oplus$ is a hydrogen or an alkali metal cation.

These brightening agents enhance the brightness in the white areas of photographic print materials.

10 Claims, No Drawings

OPTICAL BRIGHTENING AGENTS AND PHOTOGRAPHIC MATERIALS WHICH CONTAIN THESE BRIGHTENING AGENTS

This invention relates to novel optical brightening agents and to photographic materials which contain the brightening agents, for example photographic print material.

In the production of special photographic materials such as white surface-coated papers it is known to promote surface brightness by using substantially colourless blue fluorescing ultra-violet-absorbing compounds. Such compounds are in this specification denoted by the expression "brightening agents".

An important field of application of brightening agents is the manufacture of light-sensitive photographic papers; in such papers the use of brightening agents enables photograhic prints to be produced with enhanced brightness in the white areas. However many of the commercial fluorescent brightening agents suffer from the disadvantage that most of the brightening agent diffuses out of the photographic material in the steps of photographic processing and washing so that the brightening effect is lost, since they are not easily fixed nondiffusibly on a colloid of a photographic emulsion layer or auxiliary layer, for example gelatin, due to low molecular weight.

It is therefore the object of the present invention to provide novel brightening agents which can easily be incorporated into white-surface coated papers but which are not readily removed therefrom.

It is another object of the present invention to provide photographic materials having a white base and at least one silver halide emulsion layer and in one layer of the photographic material on the same side as the silver halide emulsion layer said brightening agents in a colloid binder.

It is a further object of the present invention to provide photograhic materials having a white base and at least one silver halide emulsion layer and in one layer of the photographic material on the same side as the silver halide emulsion layer a polymer formed from a latex which contains said brightening agents in a colloid binder.

Therefore according to the present invention there are provided brightening agents of the general formula

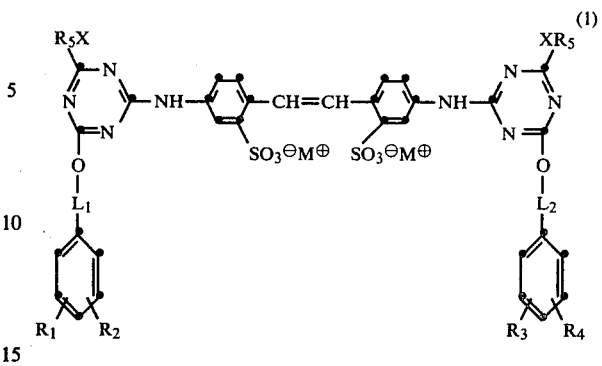

wherein $R_1$ and $R_3$ are each hydrogen or methyl, $R_2$ and $R_4$ are alkyl having at least six carbon atoms, $R_5$ is hydrogen or alkyl, aryl or aralkyl, X is —NH—, —O— or —S—, $L_1$ are each alkylene oxide chains having two to 20 alkylene oxide units in the chain and M is a hydrogen or an alkaline metal ion.

Preferably for ease of manufacture $R_1=R_3$ and $R_2=R_4$ and preferably both $R_2$ and $R_4$ have from 6 to 12 carbon atoms in the alkyl group. Examples for the alkyl group are 1,1,3,3-tetramethylbutyl, 1-methylpentyl, hexyl, neopentyl, 1-, 2- or 3-methylhexyl, heptyl, n-octyl, t-octyl, 2-ethylhexyl, n-nonyl, i-nonyl t-nonyl, decyl, t-decyl, undecyl or dodecyl. Very suitable groups $R_2$ and $R_4$ are alkyl groups having 8 or 9 atoms.

When $R_5$ is alkyl or aralkyl the alkyl moiety comprises from 1 to 8, preferably 1 to 4 carbon atoms such as methyl, ethyl, propyl or butyl and corresponding isomers; the preferred aralkyl moieties are benzyl and phenylethyl. In the meaning of aryl $R_5$ is naphthyl or phenyl, phenyl being preferred.

A suitable group X is —O— and $R_5$ is hydrogen.

$L_1$ and $L_2$ are preferably of substantially equal length in regard to the number of alkylene oxide units and are of substantially the same constitution with regard to their constituent units. However because the preferred method of manufacture of the compounds of formula (1) involves the use of nonionic wetting agents which are prepared as mixtures having an average chain length and/or constitution $L_1$ and $L_2$ may be slightly different from each other.

$L_1$ and $L_2$ are each an ethylene oxide chain of from 2 to 20 units. Examples of suitable groups $L_1$ and $L_2$ are ethylene oxide chains having from 2 to 16 or preferably from 3 to 12 or 6 to 12 units. However each may be a mixed ethylene oxide/propylene oxide chain in which the units are randomly arranged in the chain or each may comprise lengths of several ethylene oxide units joined to several propylene oxide units.

$M^\oplus$ is a hydrogen cation or an alkylene metal cation. Preferred is the hydrogen and sodium cation.

The symmetrical compounds of formula (1) where $R_1=R_3$, $R_2=R_4$ and $L_1=L_2$ may be prepared by the following three step process:

Step 1

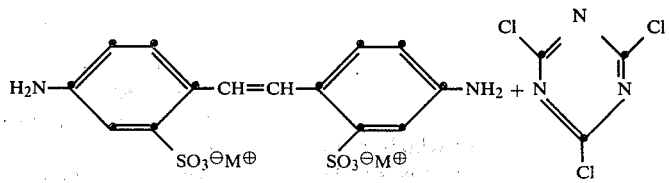

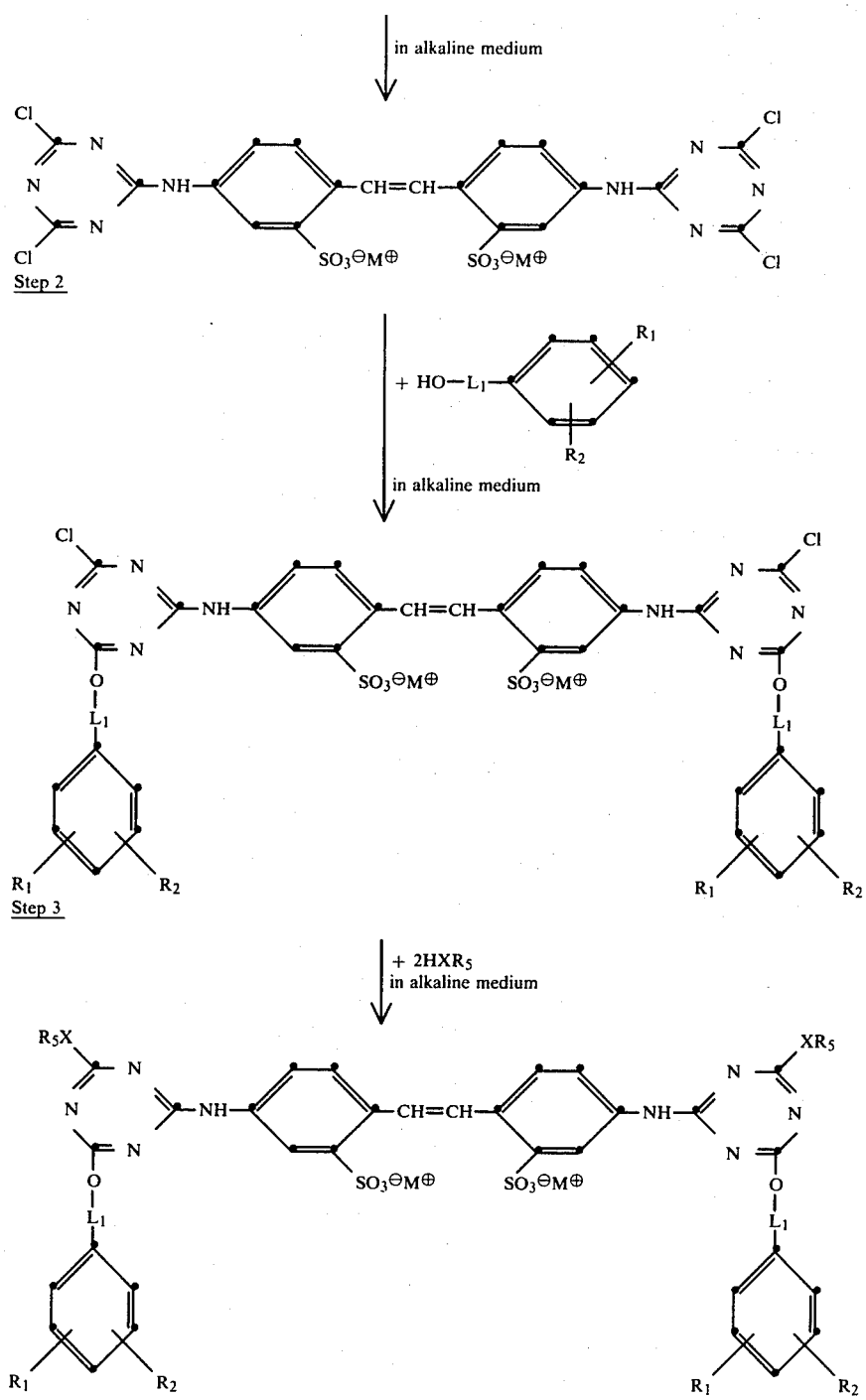
Step 2
Step 3
The compound
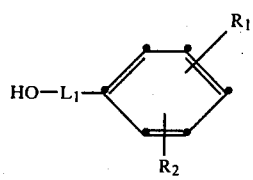
is a common nonionic wetting agent which in practice has differing alkylene oxide chain lengths. Further the position of $R_2$ on the benzene ring also is not constant. Compounds of formula (1) wherein $R_1 \neq R_3$ and $R_2 \neq R_4$ can be prepared by using a mixture of two or more different nonionic wetting agents of the general structure in step 2.

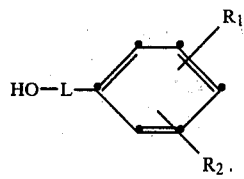

It is possible to react the alkylene oxide compound (i.e. the nonionic wetting agent) with the cyanuric chloride initially and then react the resultant compound with the stilbene disulphonic acid. However step 3 is preferably always carried out last.

According to another aspect of the present invention there are provided photographic materials having a white base and at least one silver halide emulsion layer and in one layer of the photographic material on the same side as the silver halide emulsion layer said brightening agents in a colloid binder.

The white base may be for example a baryta coated paper base, a white paper covered with a layer of polyethylene base, a white pigmented plastics film material base or polyester containing voids to render the base on opaque white diffusing base.

The preferred amount of brightening agent present in a photographic layer is from 1% to 10% based on total binder.

Preferably the brightening agent is present in the topmost layer of the photographic material above the silver halide emulsion layer or layers. However it may be present in the or any one of the silver halide emulsion layers, in the subbing layer, if present, in an intermediate layer or in the baryta layer, if present, as long as any of these layers comprise a colloid binder, for example gelatin.

The presence of the brightening agent in the photographic material leads to a marked brightening of the white areas of the print prepared from the photographic material. This brightening effect is particularly noticeable when the photographic material is black and white photographic material from which a black and white print is obtained.

Conveniently an aqueous solution of the brightening agent is added to the aqueous coating solution of the binder of the layer in which the brightening agent is to be incorporated.

Most preferably the aqueous solution of the brightening agent is added to an aqueous gelatin solution which is coated as a supercoat layer on the photographic material.

The substantivity of the brightening agents of the present invention to gelatin is good as shown in the Example which follow but it can be improved by incorporating the brightening agent into a polymer latex during the synthesis of the latex. Latexes are often incorporated into photographic assemblies partially replacing the gelatin (or other colloid) to provide greater dimentional stability and for other reasons. When the brightening agent has been incorporated in a latex which is then added to a layer of a photographic assembly the brightening agent is virtually substantive to that layer even though subjected to photograhic processing followed by prolonged washing.

Therefore according to another aspect of the present invention there are provided photographic materials having a white base and at least one silver halide emulsion layer and in one layer of the photographic material on the same side as the siler halide emulsion layer a polymer formed from a latex which comprises said brightening agents in a colloid binder.

The following Examples will serve to illustrate the invention.

EXAMPLE 1

3.7 g of 4,4'-Diaminostilbenedisulphonic acid is added to a solution of 0.8 g of sodium hydroxide in water to give a clear solution. This is added portionwise to a suspension of 3.68 g of cyanuric chloride in ice/water/acetone (prepared by addition of ice to a solution of the cyanuric chloride in 50 ml of acetone) such that the temperature does not rise above 5° C. The pH value is maintained at about 8 by addition of aqueous sodium carbonate (10 M). The mixture is stirred for a further 30 minutes maintaining a temperature of less than about 5° C. and a pH value of 8. 13 g of the compound of the formula

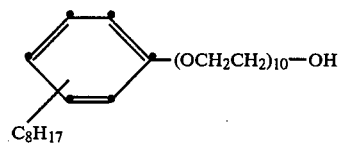

is added to the reaction mixture and the mixture stirred at room temperature overnight. The pH value is maintained at approximately 8 by addition of further aqueous sodium carbonate. 1.86 g of aniline is then added from time to time to maintain a pH value of 8. The reaction mixture is cooled and diluted with water to give a 10% solution of the compound of the formula

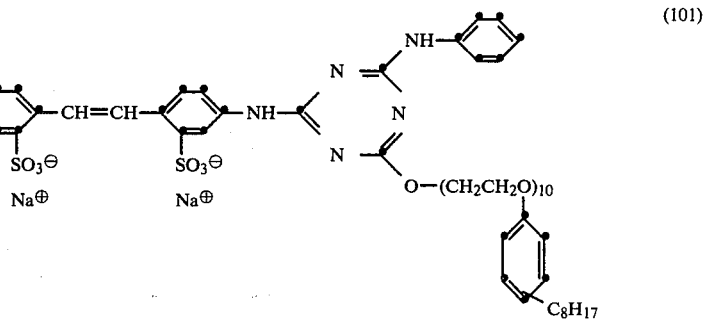

(101)

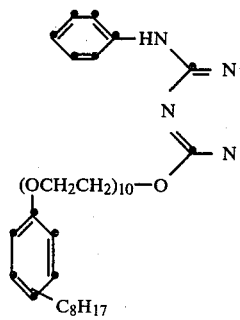

EXAMPLE 2

3.68 g of cyanuric chloride in 50 ml of acetone is treated with 50 g of ice to give a suspension. 14.4 g of a polyethylene oxide nonionic surfactant of formula

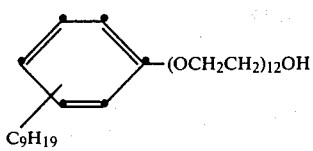

is added and the mixture stirred at a temperature of less than 5° C. for 2 hours. The pH value is maintained at 8 by addition of aqueous sodium carbonate. A solution of 4.16 g of disodium 4,4'-diaminostilbene disulphonate in water is added portionwise to the suspension with stirring, maintaining a temperature of less than 40° C. The mixture is stirred three hours at room temperature maintaining a pH value of 8 by addition of aqueous sodium carbonate. 1.86 g of aniline is then added and the mixture allowed to stand overnight. Aqueous sodium carbonate is added from time to time to maintain a pH value of about 8. The reaction mixture is refluxed 30 minutes and allowed to stand at room temperature overnight. The precipitate is filtered off and dissolved in water to give a 14% solution of the compound of the formula

EXAMPLE 4

50 ml of butyl acrylate and 50 ml of styrene are added dropwise over 1 hour to a mixture of 56 ml of 14% aqueous optical brightener of the formula (102), 30 ml of 25% aqueous anionic wetting agent, 0.4 g of sodium persulphate, 0.2 g of sodium metabisulphite and 95 ml of water, maintaining a temperature of about 65° C. After the addition of the monomer is completed, the reaction mixture is stirred at 65° C. for 3 hours. After cooling, the latex is filtered through muslin. The latex has a polymer solids content of approximately 35% and contained 8% optical brightener based on polymer level.

Using similar procedures further latexes are prepared:

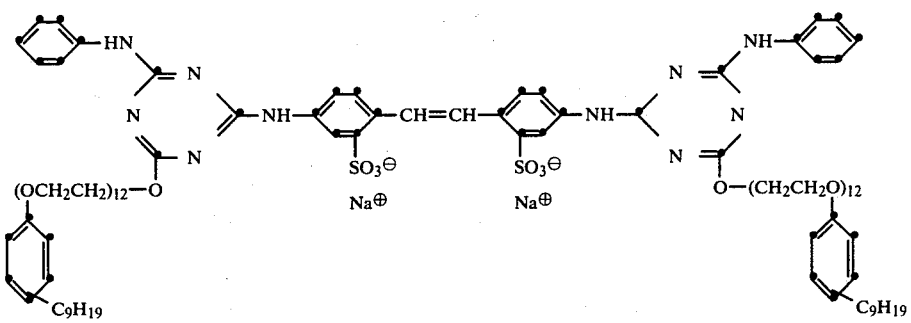

EXAMPLE 3

Using a similar procedure to those of Examples 1 and 2 the following brighteners of the formulae (103) to (108) are prepared:

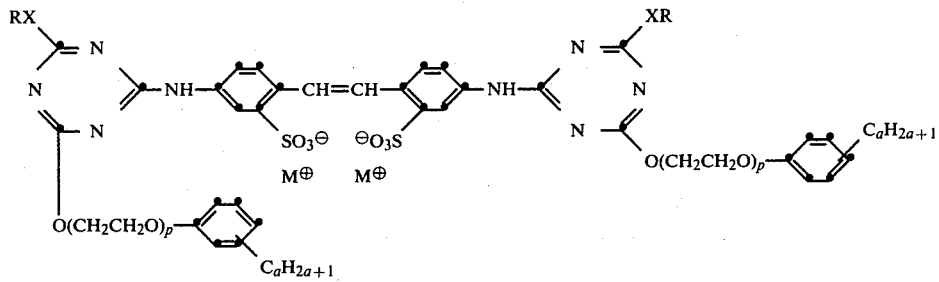

TABLE 1

| Compound | R | P | a | X |
|---|---|---|---|---|
| (103) | $C_6H_5$ | 9.5 | 9 | NH |
| (104) | H | 9.5 | 9 | O |
| (105) | $C_6H_5$ | 3 | 8 | NH |
| (106) | $C_6H_5$ | 5 | 8 | NH |
| (107) | $C_6H_5$ | 7.4 | 8 | NH |
| (108) | $C_6H_5$ | 6 | 9 | NH |

TABLE 2

| Latex Sample | Monomers | Optical Brightener Compound No. | Percentage Optical Brightener based on polymer |
|---|---|---|---|
| 109 | Butyl acrylate/styrene (1:1) | 104 | 2.5 |
| 110 | Butyl acrylate/styrene (1:1) | 103 | 1 |
| 111 | Butyl acrylate/styrene (1:1) | 103 | 3 |
| 112 | Butyl acrylate/styrene | 103 | 15 |
| 113 | Butyl acrylate/styrene (1:1) | 108 | 2.5 |
| 114 | Butyl acrylate/styrene (1:1) | 101 | 7.5 |
| 115 | Butyl acrylate/styrene (1:1) | 101 | 10 |
| 116 | Butyl acrylate/styrene (1:1) | 104 | 5 |
| 117 | Butyl acrylate/styrene (1:1) | 104 | 10 |
| 118 | Butyl acrylate/styrene (1:1) | 104 | 15 |
| 119 | Butyl acrylate/2-hydroxypropylmethacrylate (7:2) | 104 | 15 |
| 120 | Butyl acrylate/ | 102 | 7.5 |

TABLE 2-continued

| Latex Sample | Monomers | Optical Brightener Compound No. | Percentage Optical Brightener based on polymer |
|---|---|---|---|
| | styrene (1:1) | | |
| 121 | Butyl acrylate/ styrene (1:1) | 102 | 10 |
| 122 | Butyl acrylate/ 2-hydroxypropyl-methacrylate (7:2) | 107 | 7.5 |
| 123 | Butyl acrylate/ styrene (1:1) | 105 | 7.5 |
| 124 | Butyl acrylate/ styrene (1:1) | 105 | 10 |
| 125 | Butyl acrylate/ styrene (1:1) | 106 | 7.5 |
| 126 | Butyl acrylate/ styrene (1:1) | 106 | 10 |

The latexes and optical brighteners are tested by the following procedures.

Coatings are prepared using the formulation:
(a) 5 ml 6% decationised gelatin (0.3 g gelatin)
(b) 1 ml 1% triazine hardener of formula

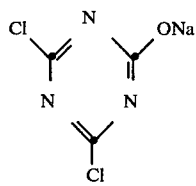

(c) 0.25 ml 1% saponin (as wetting agent)
(d) Optical brightener 1% or 1.5% w/w per 100% gelatin or Latex coated at 30% latex/70% gelatin w/w
(e) Water to 10 ml.

To determine the substantivity of the formulation, coatings are made on clear base, dried and incubated overnight. A 5 cm² disc is cut from the coating and the spectral absorption from 325 to 450 nm measured. The disc is soaked in water for periods of time up to 24 hours. Between each soaking period the disc is dried and the spectrum read.

$$\text{Substantivity} = \frac{\text{Absorbance } \lambda \text{ max after soaking}}{\text{Absorbance } \lambda \text{ max original}} \times 100\%$$

Due allowance is made for the fact that the base itself absorbs in the wavelength used.

A visual comparison of the whitening effect is also made by coating the materials on paper base.

A control is used in which 1% of Leucophor BCF (Registered Trademark) is incorporated into the gelatin layer. This compound is a non-substantive, water-soluble optical brightener. (Sample 127)

The results obtained are listed in Table 3.

| Sample compound[1] latex[2] | Conc. w/w | % substantivity after different soaking times | | | |
|---|---|---|---|---|---|
| | | 30 min. | 1 hr | 6 hr | 24 hr |
| 101 | 1% | 52 | 43 | 33 | 29 |
| 102 | 1% | 44 | 26 | 19 | 15 |
| 103 | 1.5% | 62 | 40 | 32 | 29 |
| 104 | 1.5% | 78 | 71 | 67 | 67 |
| 105 | 1.5% | 82 | 50 | 34 | 15 |
| 106 | 1.5% | 100 | 50 | 35 | 5 |
| 107 | 1% | 71 | 51 | 42 | 35 |
| 108 | 1% | 77 | 71 | 66 | 54 |
| 109 | 1.1% | 63 | 63 | 31 | 31 |
| 110 | 0.4% | 93 | 93 | 93 | 93 |
| 111 | 1.3% | 85 | 77 | 70 | 64 |
| 112 | 6.4% | 83 | 52 | 37 | 24 |
| 113 | 1.1% | 74 | 74 | 74 | 74 |
| 114 | 3.2% | 85 | 80 | 75 | 75 |
| 115 | 4.3% | 85 | 78 | 73 | 71 |
| 116 | 2.1% | 52 | 52 | 52 | 52 |
| 117 | 4.3% | 62 | 52 | 52 | 52 |
| 118 | 6.4% | 79 | 67 | 59 | 59 |
| 119 | 6.4% | 50 | 47 | 44 | 42 |
| 120 | 3.2% | 68 | 58 | 54 | 54 |
| 121 | 4.3% | 88 | 70 | 62 | 51 |
| 122 | 3.2% | 77 | 69 | 67 | 65 |
| 123 | 3.2% | 84 | 69 | 62 | 54 |
| 124 | 4.3% | 88 | 72 | 64 | 55 |
| 125 | 3.2% | 87 | 81 | 75 | 75 |
| 126 | 4.3% | 87 | 80 | 73 | 71 |
| 127 (comparison) | 1% | 58 | 35 | 9 | 4 |

[1]samples 101 to 108, 127, (gelatin)
[2]samples 109 to 126, (30:70 latex/gelatin)

It is to be noted that it is common practice to allow photographic prints to wash overnight. Thus it is required that the substantivity of the brightening agent is such to prevent it being washed out after up to 24 hours washing.

I claim:

1. A brightening agent of the general formula

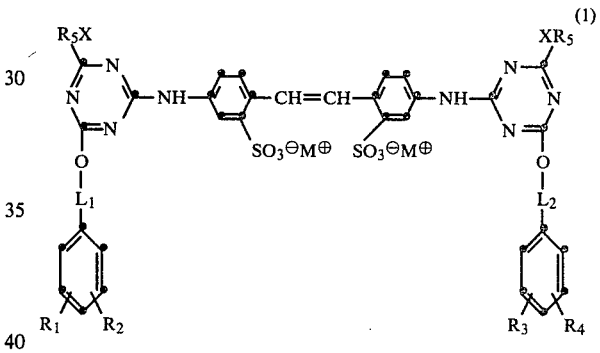

wherein $R_1$ and $R_3$ are each hydrogen or methyl, $R_2$ and $R_4$ are alkyl having at least six carbon atoms, $R_5$ is hydrogen or alkyl, aryl or aralkyl, X is —NH—, —O— or —S—, $L_1$ and $L_2$ are each alkylene oxide chains having two to 20 alkyene oxide units in the chain and $M^{\oplus}$ is a hydrogen or an alkylene metal cation.

2. A brightening agent according to claim 1 wherein $R_1=R_3$ and $R_2=R_4$.

3. A brightening agent according to claim 1 wherein both $R_2$ and $R_4$ have 6 to 12 carbon atoms in the alkyl chain.

4. A brightening agent according to claim 1 wherein both $R_2$ and $R_4$ have 8 or 9 carbon atoms in the alkyl chain.

5. A brightening agent according to claim 1 wherein X is —NH— and $R_5$ is alkyl or aralkyl the alkyl moiety having 1 to 8 carbon atoms, or $R_5$ is aryl.

6. A brightening agent according to claim 1 wherein X is —NH— and $R_5$ is alkyl or aralkyl the alkyl moiety having 1 to 4 carbon atoms or $R_5$ is naphthyl or phenyl.

7. A brightening agent according to claim 6, wherein X is —NH— and $R_5$ is phenyl.

8. A brightening agent according to claim 1 wherein X is —O— and $R_5$ is hydrogen.

9. A brightening agent according to claim 1 wherein $L_1$ and $L_2$ are each an ethylene oxide chain of from 2 to 16 ethylene oxide units.

10. A brightening agent according to claim 1 wherein $L_1$ and $L_2$ are each an ethylene oxide chain of from 6 to 12 ethylene oxide units.

* * * * *